United States Patent
Kay et al.

(10) Patent No.: US 7,799,061 B2
(45) Date of Patent: Sep. 21, 2010

(54) ORTHOPEDIC PLATE

(75) Inventors: David B. Kay, Akron, OH (US); Lee A. Strnad, Broadview Hts., OH (US); Dustin Ducharme, Akron, OH (US); G. Martin Wynkoop, Gainsville, FL (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 498 days.

(21) Appl. No.: 11/340,027

(22) Filed: Jan. 26, 2006

(65) Prior Publication Data

US 2006/0200145 A1  Sep. 7, 2006

Related U.S. Application Data

(60) Provisional application No. 60/691,171, filed on Jun. 16, 2005, provisional application No. 60/648,364, filed on Jan. 28, 2005.

(51) Int. Cl.
*A61B 17/80* (2006.01)
(52) U.S. Cl. .................. 606/283; 606/280; 606/286
(58) Field of Classification Search .......... 606/280, 606/71, 283–285, 298, 299
See application file for complete search history.

(56) References Cited

U.S. PATENT DOCUMENTS

| | | | |
|---|---|---|---|
| 1,105,105 A * | 7/1914 | Sherman | 606/286 |
| 2,526,959 A | 10/1950 | F.A. Lorenzo | |
| 3,716,050 A | 2/1973 | Johnston | |
| 4,867,144 A | 9/1989 | Karas et al. | |
| 4,903,691 A * | 2/1990 | Heinl | 606/70 |
| 4,959,065 A * | 9/1990 | Arnett et al. | 606/86 B |

(Continued)

FOREIGN PATENT DOCUMENTS

CH      611147 A5    5/1979

(Continued)

OTHER PUBLICATIONS 6 pages from the Reconstructive Surgery Product Catalog 2005 INTEGRA™ new deals®, New ideas for foot surgery™, including p. 18 Newdeal-Hallu®-Fix.

(Continued)

*Primary Examiner*—Eduardo C Robert
*Assistant Examiner*—Ellen C Hammond
(74) *Attorney, Agent, or Firm*—Hudak, Shunk & Farine Co. LPA

(57) ABSTRACT

The present invention relates to an orthopedic plate and screw system and instruments for surgical fixation of a small bone or bones including specifically the small bones of the spine. The plate facilitates three dimensional contouring to provide for a variety of applications and to accommodate individual variation in bone shape. The plate has a modified x shape including a central trunk portion including one or more screw holes along a longitudinal axis and a set of divergent upper and an oppositely extending set of divergent lower arms, each arm including screw holes which are placed at a radially equal distance but which diverging asymmetrically from the longitudinal axis relative to its paired upper or lower mate. The screws of the system are self-starting, self-tapping screws including the option of partial or full cannulation. In a further embodiment, the plate is intended for use through the length of the spine.

24 Claims, 6 Drawing Sheets

U.S. PATENT DOCUMENTS

| | | | |
|---|---|---|---|
| 5,290,281 A * | 3/1994 | Tschakaloff | 606/28 |
| 5,304,180 A | 4/1994 | Slocum | |
| 5,324,290 A | 6/1994 | Zdeblick et al. | |
| 5,459,298 A * | 10/1995 | Tschakaloff | 219/227 |
| 5,607,427 A * | 3/1997 | Tschakaloff | 606/284 |
| 5,681,311 A | 10/1997 | Foley et al. | |
| 5,690,631 A * | 11/1997 | Duncan et al. | 606/281 |
| 5,718,705 A | 2/1998 | Sammarco | |
| 5,749,872 A | 5/1998 | Kyle et al. | |
| 5,779,706 A * | 7/1998 | Tschakaloff | 606/281 |
| 5,827,286 A * | 10/1998 | Incavo et al. | 606/71 |
| 5,853,413 A * | 12/1998 | Carter et al. | 606/281 |
| 6,030,389 A | 2/2000 | Wagner et al. | |
| 6,096,040 A | 8/2000 | Esser | |
| 6,123,709 A | 9/2000 | Jones | |
| D449,692 S | 10/2001 | Michelson | |
| 6,348,052 B1 * | 2/2002 | Sammarco | 606/284 |
| 6,358,250 B1 | 3/2002 | Orbay | |
| 6,454,769 B2 | 9/2002 | Wagner et al. | |
| 6,527,776 B1 | 3/2003 | Michelson | |
| 6,565,570 B2 | 5/2003 | Sterett et al. | |
| 6,565,571 B1 * | 5/2003 | Jackowski et al. | 606/86 B |
| 6,575,975 B2 | 6/2003 | Brace et al. | |
| 6,585,769 B1 | 7/2003 | Muhanna et al. | |
| 6,652,530 B2 * | 11/2003 | Ip et al. | 606/284 |
| 6,960,211 B1 * | 11/2005 | Pfefferle et al. | 606/282 |
| D520,637 S | 5/2006 | Kay et al. | |
| 7,052,499 B2 * | 5/2006 | Steger et al. | 606/291 |
| 7,108,697 B2 * | 9/2006 | Mingozzi et al. | 606/297 |
| 7,128,744 B2 | 10/2006 | Weaver et al. | |
| 7,166,111 B2 * | 1/2007 | Kolb et al. | 606/96 |
| 7,288,095 B2 * | 10/2007 | Baynham et al. | 606/288 |
| 7,335,204 B2 * | 2/2008 | Tornier | 606/284 |
| 2003/0199875 A1 | 10/2003 | Mingozzi et al. | |
| 2004/0193163 A1 | 9/2004 | Orbay | |
| 2005/0015089 A1 | 1/2005 | Young et al. | |
| 2005/0192577 A1 * | 9/2005 | Mosca et al. | 606/69 |
| 2006/0106387 A1 * | 5/2006 | Fanger et al. | 606/69 |
| 2006/0122607 A1 * | 6/2006 | Kolb | 606/71 |
| 2006/0129151 A1 | 6/2006 | Allen et al. | |
| 2006/0173458 A1 | 8/2006 | Forstein et al. | |
| 2006/0173459 A1 | 8/2006 | Kay et al. | |
| 2006/0200145 A1 | 9/2006 | Kay et al. | |
| 2006/0229610 A1 * | 10/2006 | Piehl | 606/61 |
| 2007/0073298 A1 | 3/2007 | Beutter et al. | |
| 2007/0173840 A1 * | 7/2007 | Huebner | 606/69 |
| 2007/0185493 A1 | 8/2007 | Feibel et al. | |
| 2008/0300632 A1 | 12/2008 | Butler et al. | |
| 2008/0300637 A1 | 12/2008 | Austin et al. | |

FOREIGN PATENT DOCUMENTS

| | | |
|---|---|---|
| DE | 203 09 361 U1 | 5/1979 |
| EP | 1 468 655 A2 | 10/2004 |
| FR | 2 233 973 A1 | 2/1975 |
| FR | 2 405 062 A1 | 6/1979 |
| FR | 2 405 705 A1 | 6/1979 |
| FR | 2 405 706 A1 | 6/1979 |
| JP | 11299804 | 11/1992 |
| WO | WO 02/096309 A1 | 12/2002 |

OTHER PUBLICATIONS 4 pages from the INTEGRA™ Jan. 2005 new deal®, Hallu®-S PLATE.
Locking Clavicle Plate System by ACUMED® Jul. 2005, (7 pages).
3.5 mm LCP Superior Anterior Clavicle Plates, by SYNTHES® Sep. 2008 (24 pages).
PERI-LOC Locked Plating System—Clavicle Locking Plate by Smith&Nephew, May 2007 (16 pages).
Locking Bone Plate System for Hallux-Valgus Corrections "Opening or Closing Base Wedge" Osteotomy by MetaFix™ Feb. 2005 (2 pages).
TOM™-Platte by DARCO® Innovation in Foot Care Technology, Dec. 8, 2006 (2 pages).
New Trauma Products from AO Development, Jun. 2006 (p. 6).
4 pages from INTEGRA™ Jan. 2005 new deal®, Hallu®—S PLATE.

* cited by examiner

ORTHOPEDIC PLATE

CROSS-REFERENCE

This application claims the benefit of priority under 35 U.S.C. §119 of U.S. Provisional Application Ser. No. 60/691,171 filed on June 16, 2005 and U.S. Provisional Application Ser. No. 60/648,364 Jan. 28, 2005

FIELD OF THE INVENTION

The present invention relates to an orthopedic plate for surgical repair or reconstruction of a bone in instances where it is desirable to have convergent screw fixation with screws that placed by the plate so as to be unlikely to impinge on each other.

BACKGROUND OF THE INVENTION

The field of orthopedic medicine has grown tremendously in the past fifty years as surgical techniques, implants and instrumentation have developed and been improved. The medical companies have tended to focus their attention on the largest market areas so that some areas of the body, such as the spine, knees and hips, have received intense focus from the large medical companies. While the small bones are frequently subject to the need for re-constructive surgery for example, as a result of trauma, to counteract the effects of aging or to repair congenital deformities, this area has typically not received the same degree of attention from the medical companies as joint replacement, trauma and spinal areas. Consequently, the products available to the small bone surgeon often represent scaled down versions of products designed for the large long bone market which are not adequate for the fine bones and delicate procedures required of the small bone surgeon. Additionally, while there is a wide variety in the exact shape and mass of all bones, these variations become more problematic in providing orthopedic implants for small bone applications since there is less room on and about the bone for the surgeon to place and fix the construct. These bones are finer and have less surface area for placement of an implant, and less mass for the placement of screws and as a result, individual variations become more problematic for implants of stock design.

While some of the spinal companies have focused on hardware intended for use in the cervical and thoracic areas of the spine, some of the same problems exist in these areas as have been previously listed, thus the present invention is also useful in a slightly modified, and more robust form for use in the spine.

One problem that needs to be avoided in the delicate environment of the congested bone area, such as the metacarpals, the metatarsals, and the cervical region of the spine, is the interference of screws, with other screws, and with the function of ligaments and tendons. It may be desirable to design an orthopedic plate so that securing screws converge in order to cause compression or increase the pullout strength, it is difficult when a screw impinges on or conflicts with the desired placement of another screw. Some surgeons prefer bicortical fixation in which a screw is sized so that the distal end is secured in cortical bone giving the screw better purchase, however, other surgeons may prefer to avoid placing a screw so that it projects beyond the outer surface of the anchoring bone. These factors are complicated by the relative lack of soft tissue and the presence of ligaments and tendons in these small or congested bone areas. Consequently, the less forgiving biological environment in which the small bone or cervical surgeon works requires greater procedural precision and calls for specialized implants and tools.

The present invention is designed to meet the specific needs of the small bone surgeon to facilitate effective and repeatable procedures which provide for ease of use and a range of function for this specific area of specialization. The present invention could serve for the treatment of a broad range of indications including relatively straightforward fracture repair following trauma in an otherwise healthy individual where screws are used alone or with plates to maintain the integrity of the bones while they heal, as well as for more complex surgeries such as reconstruction to correct congenital or age related deformation. Reconstruction often includes arthrodesis or partial or total fusion which involves removal of a joint and the use of a mechanical-biological construct to keep the bones immobile while fusion occurs. Further small bone surgeons may be called upon to achieve soft-tissue balancing by readjusting the length of tendons and ligaments or to reshape the bone itself through removal or repositioning in a procedure known as an "ostetomy". In an aging or diabetic population, these procedures may also involve dealing with the difficulties of poor quality bone and/or compromised soft tissue.

These surgeons typically include sub-specialists such as hand surgeons and feet and ankle and podiatric surgeons, but can also include general orthopedic surgeons who may be called upon to perform procedures on the small bones.

The present invention provides a plate with asymmetrical and bi-planar screw fixation and further designed to facilitate three dimensional contouring to provide for a variety of applications and to accommodate individual variation in bone shape. The plate is designed specifically for the small bone market, i.e. for use in bones distal to the elbow and knee, including, for example, the ulna, radius, tibia, fibula, as well as the metacarpals, carpals, metatarsals, tarsals, and phalanges, and in a further embodiment for the spine. The plate can be used in applications previously mentioned, for example those that require fixation to a single bone such as the stabilization of a fracture or the plate can be used across two or more bones so as to facilitate total or partial fusion. The plate is configured to bend laterally, longitudinally, and to wrap or spiral about its longitudinal axis so that it can be molded to an optimal shape for small bone procedures. The plate is designed to provide optimal stabilization of fractures and osteotomies by providing multi-planar fixation that allows for better pull-out and limited axial loading to the bone. The plate is further designed to accelerate fusion success by reducing or eliminating torsional or twisting stresses to the bone segments during the healing process. In addition, when desired, the plate can be shaped so as to apply a compressive, or even a tensile, force, for example, along the longitudinal axis of a bone.

The plate has a central trunk portion including one or more screw holes separated by a waist shaped linking portion along a longitudinal axis and a set of upper and lower arms including screw holes which are placed at a radially equal distance but which diverge asymmetrically from the longitudinal axis to avoid conflicts in the screw placement of the paired arm, specifically, so that the screws of a set of arms do not impinge on each other. The plate is radiused with a curvature corresponding generally to the curvature of a bony surface. The upper pair of arms, and the lower pair of arms continue this curvature and the through holes are placed so that the angle of the longitudinal axis of the screws converge in the direction of the distal end of the screw. The screw holes are placed with the longitudinal axis perpendicular a tangent to the top surface of the arm with the effect that the longitudinal axes of the screws converge in the direction of the distal end. This increases the pull-out strength of the screws. Further the screw holes are concavely rounded to allow for multi-axis orientation of the low profile, rounded screw in the hole, which can be oriented with a conical shape about the longitudinal axis of the screw hole having an angle of at least 20°, preferably at least 25°, and most preferably about 30°.

The screws do not in fact conflict since each of the arms in a pair form a different angle to the central trunk so that the longitudinal axis of the screws are offset from each other along the length of the plate. The pre-bent configuration of the plate is designed to increase operating room efficiency by facilitating commonly desirable shapes while maintaining the required strength and by permitting bending without deforming the screw holes. This results in making customization in anticipation or during surgery easier.

The screws useful with the plate of the present invention are self-starting, self-tapping screws including the option of partial or full cannulation. The screws include a cutting end having multiple flutes, and preferably 2 or 3 flutes about a conical recess. The screws further include a partial taper of the inner diameter in the proximal end over the first several thread turns, for example over 2-8, and preferably over 3-5 turns in order to increase the fatigue life of the screw as well as providing potential physiological advantages in use. The screw head is a rounded low profile head. The screws further include a torque driving recess that may be a hexagon, a torx shape, or a modification of a torx shape, i.e. a multilobe shape having from 3 to 12 lobes, and preferably having 4 to 8 rounded recesses or lobes. The recess can be of a constant size in the direction of the longitudinal axis, or can taper inward along the longitudinal axis of the screw toward the bottom of the recess.

The instruments for use with the system are well-balanced and ergonomically designed with sufficiently long handles to place the surgeon's hands outside of the line of radiation and designed to reduce fatigue in the operating room.

The plate system of the present invention is thus designed to fit a range of needs of the surgeon operating on the small bones (specifically including the small bones of the spine) to allow him or her to perfect a variety of techniques using a set of instruments and a customizable plate and screw construct.

DETAILED DESCRIPTION OF THE INVENTION

Figure 1:
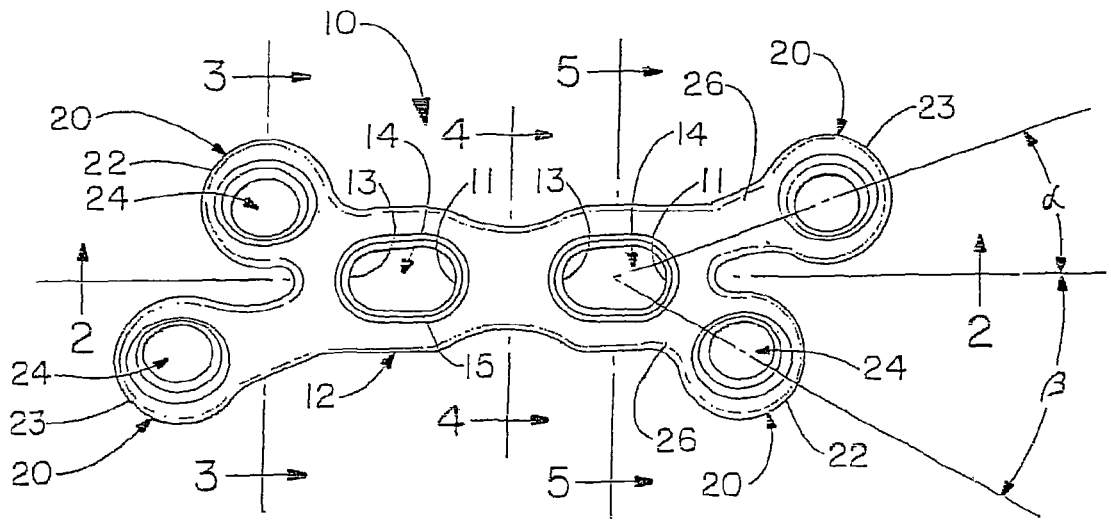
FIG. 1 is a top view of an alpha orthopedic plate in accordance with the invention.

The plate 10 of the present invention is shown having a asymmetric shape which can be thought of as being similar to the Greek letter χ with foreshortened opposing diagonal legs extending from a central trunk portion 12 defining the longitudinal axis of the plate. The trunk portion 12 includes one or preferably more screw holes 14 along the longitudinal axis. The number of screw holes in the trunk portion 12 will depend on the length of the plate, and may range from 0 to 6, and more preferably from 2 to 4. In one embodiment the holes are compression holes. The screw holes 14 are preferably slotted or elongated with a larger radius area 11 on each of the screw holes facing in the same direction, and a smaller radius area 13 which has a shallower lip to allow the plate to be set initially and subsequently to be slide into a different position as the screws are tightened down. This allows compression to be applied across the middle of the trunk section. Further, the screw holes include annular rings 15 of increased thickness in the vertical direction about through holes 14.

The through holes 14 in the trunk portion 12 have a longitudinal axis that is perpendicular to plane tangent to the top radius of the plate. The area linking the screw holes has a decreased width so as to define a waist area 26 that will bend laterally (or "curve") relative to the longitudinal axis and which will bend longitudinally to form a curved area in and out of the plane of the plate. This thinner area also facilitates twisting of the plate so as to allow the plate to spiral, or wrap around it longitudinal axis. The increased annular area around the through bores resists deformation when a bending device is used to apply a force to the plate through the screw holes.

The plate 10 also includes at least one set, and preferably two opposing sets of arms 20. As viewed in FIG. 1, these sets of arms can be viewed as a set of upper and lower arms, although it is understood that the orientation of the plate can vary even after the plate has been fixed to the bone so that the terms upper and lower are only used to distinguish the pair on one side of the trunk portion 12 from the pair on the other side of the trunk portion 12. The arms can also be thought of as a first 22 and second 23 set of diagonally opposing arms which correspond in shape and size. The plate is bilaterally asymmetrical, meaning that the right half and the left half are not the same. Neither is the top of the plate the same as the bottom half of the plate, but the plate has a transverse mirror symmetry, meaning that while they are not the same, the half on one side of a transverse plane if a mirror image of the half on the other side of the plane. This means that the plates exhibit a handedness, and are presented as an alpha and a beta version, which correspond roughly to a left and right version. It should also be understood that the plates can have a single set of arms at one end of the plate and a truncated trunk portion. Each of the arms in a set includes screw holes 24 which are placed at a radially equal distance but which diverging asymmetrically from the longitudinal axis of the plate 10. More specifically, each set of arms includes one arm that defines a smaller angle of divergence α from the longitudinal axis of the trunk portion than the angle of divergence of the other arm β. For example, the first angle shown in FIG. 1 at α may be from about 5° to about to 25°, and more preferably from about 10° to about to 20° and most preferably from about 12° to about to 16°, while the second angle shown at β from about 10° to about to 35°, and more preferably from about 15° to about to 30° and most preferably from about 22° to about to 26° with a preferred difference in the angles beings from about 2° to about to 20°, and more preferably from about 4° to about to 16° and most preferably from about 8° to about to 12°.

In addition to the angled arms of this asymmetrical dog-bone shape facilitating a variety of useful positions in the small bone area, the plate of the present invention is sized to fie the needs of the small bone specialist. For small bone usage, the total length of the plate along its longitudinal axis is from about 25 mm to about 80 mm, depending on the number of screw holes in the trunk portion. The total width is from about 12 mm to about 18 mm, width an inferior radius of curvature of about 8 mm to about 12 mm and a concentric radius on the superior side. Typically, the waist area measures from about 7.5 mm to about 10 mm from the center of the larger, i.e. about 3.8 mm, radiused portion of the holes. The trunk portion has a width of about 7 mm to about 9 mm wide at the wider parts and about 3 mm to about 5 mm wide at the narrower waist portion. The longer arm has a length along the longitudinal axis of the plate from the center of the screw hole to the center of the plate for a two-hole trunk of from about 12 mm to about 16 mm, with a width of about 3 mm to about 5 mm. The shorter arm has a comparable length of from about 7 mm to about 15 mm with a narrowed width of about 2.5 to about 5 mm. In a further embodiment the plate could be modified for use in the long bones with a length of up to about 400 mm with a width of up to about 50 mm, and proportional sizes for the arms and thickness.

On the inferior side, or the side that would be facing the bone surface in use, the arms continue the radius of curvature of the trunk portion. The superior or top side of the plate has a similar radius of curvature as the top surface of the plate has an outline that corresponds with the shape of the bottom of the plate (excluding the optional thickened annular area surrounding the screw holes which would act to shield these holes against deformation during bending.) The screw holes also include a rounded concavity to mate with the rounded shape of the head of the screw to allow of variable axis positioning. The screw holes 24 are placed with the longitudinal axis perpendicular a tangent to the top surface of the arm with the effect that the longitudinal axes of the screws converge in the direction of the distal end. This increases the pull-out strength of the plate/screw construct. Since the arms are asymmetrical relative to each other, and in particular since they diverge from the longitudinal axis of the trunk portion at differing angles, conflicts in the positions of paired screws is avoided so that the screws of a set of arms typically do not impinge on each other. This is even more important in instances where the plate is bent around the longitudinal axis so as to wrap around the longitudinal axis of the bone.

Figure 2:
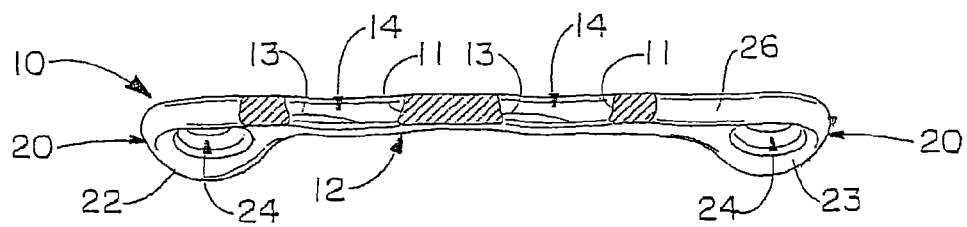
FIG. 2 is a cross-section of the plate taken along line 2-2.
Figures 3, 4, 5:
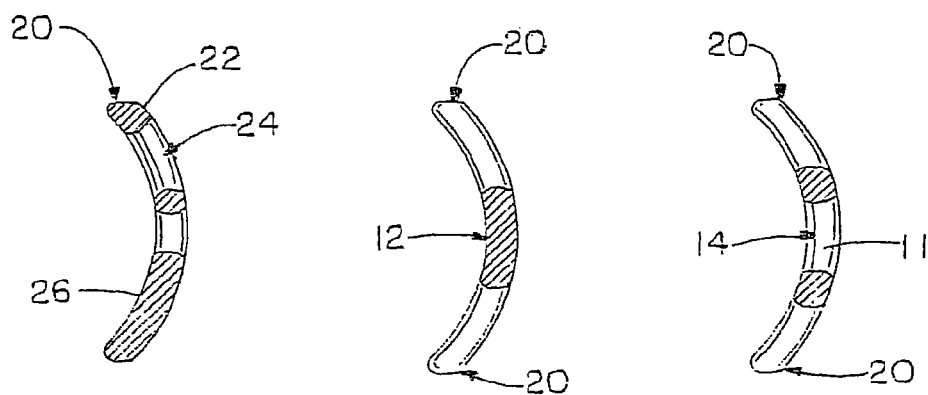
FIG. 3 is a cross-section of the plate taken along line 3-3.
FIG. 4 is a cross-section of the plate taken along line 4-4.
FIG. 5 is a cross section of the plate taken along line 5-5.
Figure 6:
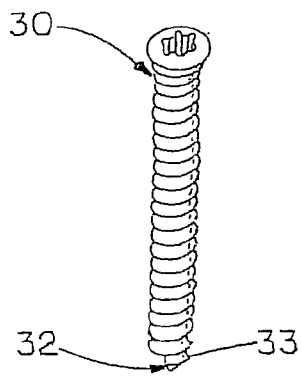
FIG. 6 is a perspective view of a screw used with the present system.
Figure 7:
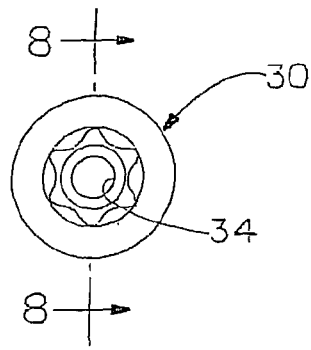
FIG. 7 is a detail of the torque receiving recess of the screw shown in FIG. 6.
Figure 8:
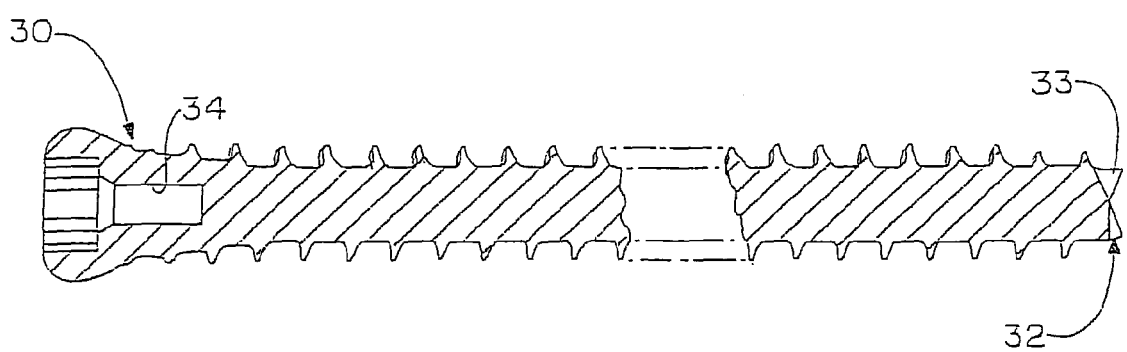
FIG. 8 is a cross-section of the screw of FIG. 6 taken along line 6-6.

The arms 20 also each include a screw hole 24 which, like the trunk portion 12 has a linking portion 26 that joins the screw hole to the trunk portion. Again this design facilitates the desired bending while resisting deformation of the screw holes 24 when they are used with the bending instrument to contour the plate. While the angle of the arms 20 of each one of a pair of a respective set of arms 22 and 23 varies so as to create a bilateral asymmetry, meaning that the plate is not symmetrical with respect to a plane that passes through the longitudinal axis in the vertical direction from the superior (the top side relative to the bone) to the inferior side (the side facing the bone), the "first plane". However, the position of the arms in each set is preferably flipped so that the symmetry of the plate shape about a plane transverse to the first plane is a mirror image, this is defined herein as transverse mirror symmetry. The screws holes of the trunk portion can include means to induce a compressive force in one direction, such as a ramped area on each screw hole. These ramped areas would be ramped on the same side of the holes looking down from the top of the plate. Typically the first screw implanted stabilizes and the second screw is used to achieve compression. Further the length of each of the arms of a pair will vary so that the radial length of the center of the screw hole to the intersection with the longitudinal axis will be the same. As shown in FIGS. 2-4, the plate includes a radial curve about the longitudinal axis. The radius is typically about 10 mm with a transverse dimension from the edge of one arm to the edge of the other arm of an upper or lower pair being about 15 or 16 mm for typical small bone usage, and the screw bore having a longitudinal axis of about 24° to an plane passing through the longitudinal axis of the plate. The bores are typically about 3.75 mm for a 3.5 mm diameter screw for small bones excluding the smallest of applications which would include phalanges. Again, for the smallest application as well as long bone embodiments the screws and corresponding screw holes could be sized to range from a 1.5 mm diameter screw up to a 7.5 mm diameter screw. In a further embodiment, the bore could be threaded.

FIG. 4 shows a screw 30 used with the plate system of the present invention. The distal end of the screw includes a cutting tip 32 which is self-starting and self-tapping. This aspect is defined by a conical recess and a plurality of flutes 33. These screws 30 can optionally include partial or full cannulation 34. The head of the screw is spherical and includes a torque driving recess, such as a modified multilobe shape as is shown in FIG. 5. The screw has a cancellous thread with a constant major diameter and a minor diameter that tapers proximally in order to increase fatigue life of the screw and to improve compression and compensate for bone resorption.

Figure 9:
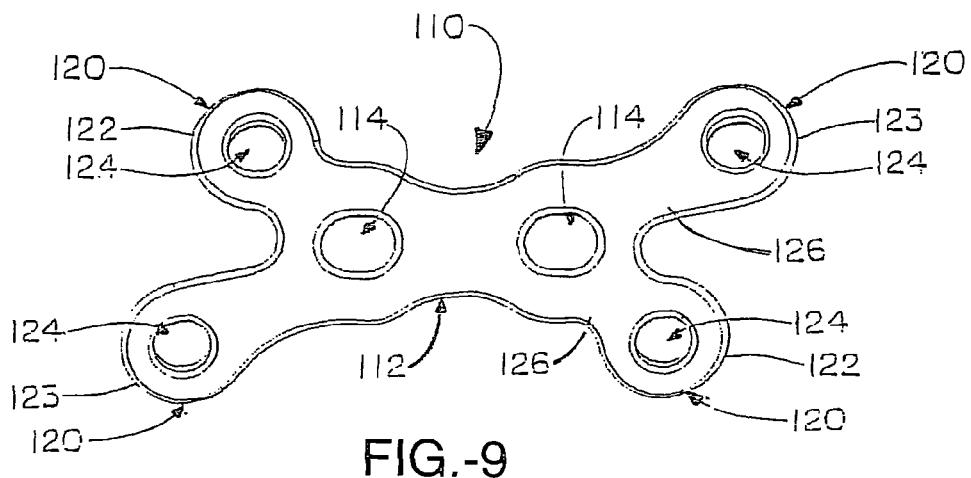
FIG. 9 is a top view of a second embodiment of an orthopedic plate in accordance with a further aspect of the invention.

An additional embodiment of the plate in accordance with the present invention is shown in FIG. 9. This plate 110 shares the same features as the design show in FIG. 1, but is somewhat more robust, with less tapering at the trunk portion 112. The plate includes opposing pairs of asymmetrical arms, 120, which can again be viewed as upper 122, and lower 123 arms, each including a set of screw holes 124 The trunk area 112 further includes slotted screw holes 114 which can be similarly used to cause a compression between them. The bottom side is radiused as for the small bone area, but with a gentler curvature of radius.

Figure 10:
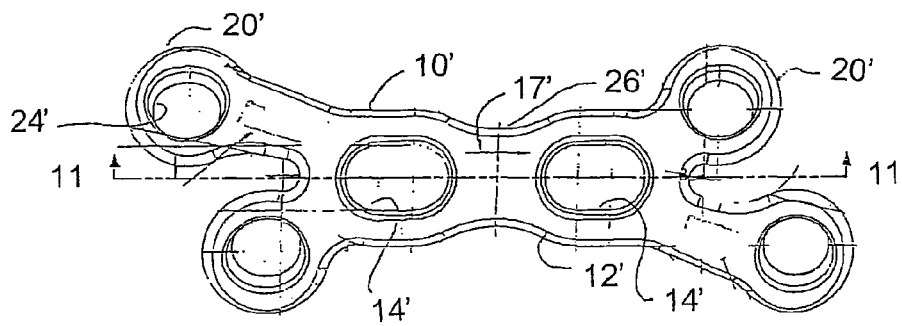
FIG. 10 is a top view of a beta version of the first embodiment of a plate in accordance with the invention.
Figure 11:
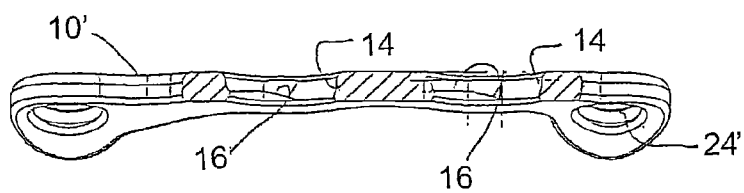
FIG. 11 is a cross section of the plate of FIG. 10 taken along line 11-11.

FIG. 10 is a beta version of the plate shown in FIG. 1. Thus, it is a mirror image of the plate, with corresponding elements such as a trunk portion 12', a pair of angled arms 20' at either end each having a screw hole 24', and the trunk portion 12' having two compression slots 14' that can be used to apply a compressive force in the direction indicated by the arrow 17' by placing the screw near the front of the slot, or can be used at a neutral compression by placing the screw in the middle of the slot when they are first put in. FIG. 11 is a cross-section of the plate of FIG. 10.

Figure 13:
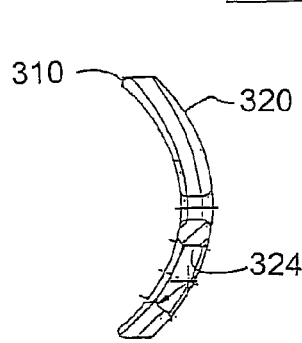
FIG. 13 is a cross section of the plate of FIG. 12 taken along line 13-13.
Figure 12:
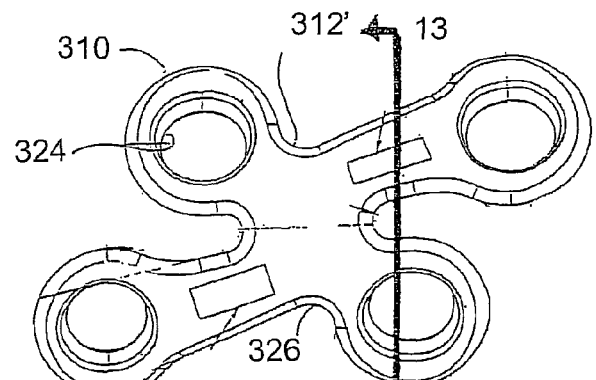
FIG. 12 is a top view of an alpha version of a third embodiment of a plate in accordance with the invention.
Figure 15:
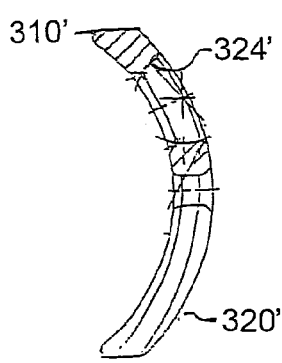
FIG. 15 is a cross section of the plate of FIG. 14 taken along line 15-15.
Figure 14:
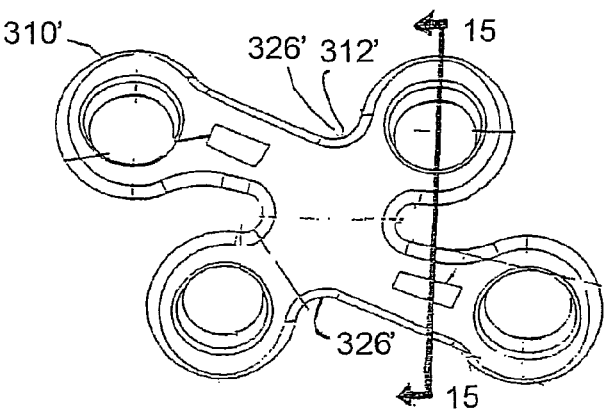
FIG. 14 is a top view of a beta version of the third embodiment of a plate in accordance with the invention.
Figure 16:
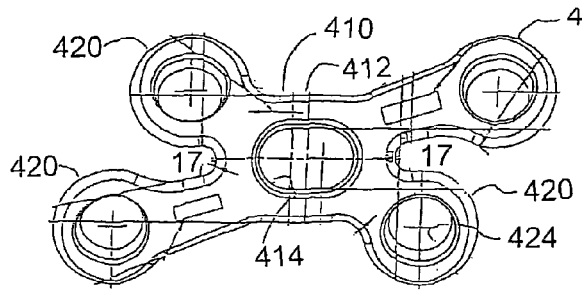
FIG. 16 is a top view of an alpha version of a fourth embodiment of a plate in accordance with the invention.
Figure 18:
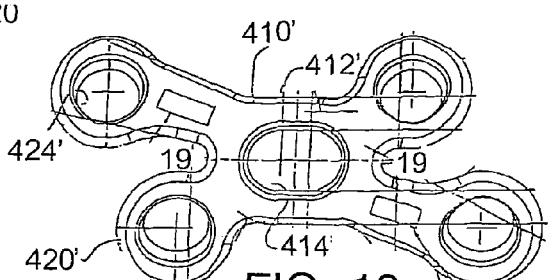
FIG. 18 is a top view of the beta version of the fourth embodiment of the plate in accordance with the invention.
Figure 17:
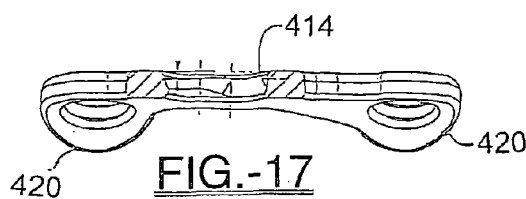
FIG. 17 is a cross section of the plate of FIG. 16 taken along line 17-17.
Figure 19:
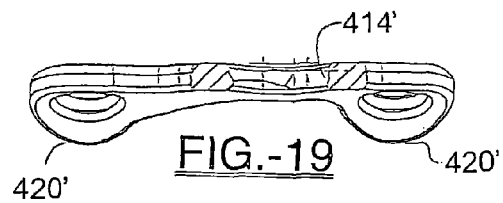
FIG. 19 is a cross section of the plate of FIG. 18 taken along line 19-19.
Figure 20:
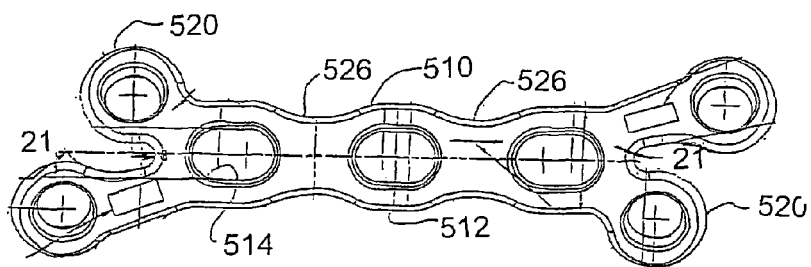
FIG. 20 is a top view of an alpha version of a fifth embodiment of a plate in accordance with the invention.
Figure 21:
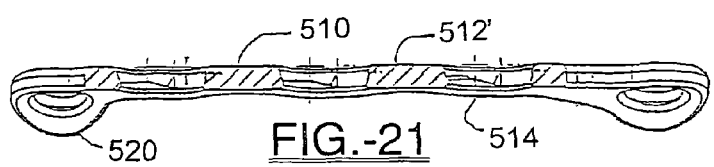
FIG. 21 is a cross section of the plate of FIG. 20 taken along line 21-21.
Figure 22:
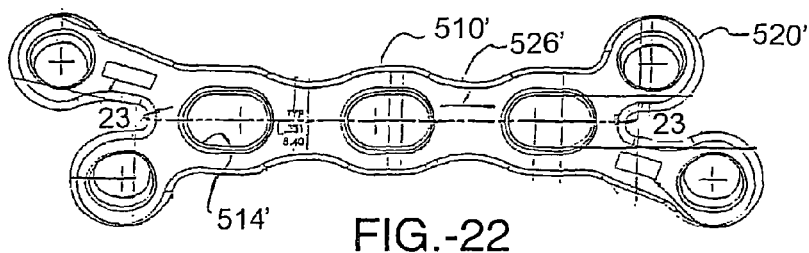
FIG. 22 is a top view of the beta version of the fifth embodiment of the plate in accordance with the invention.
Figure 23:
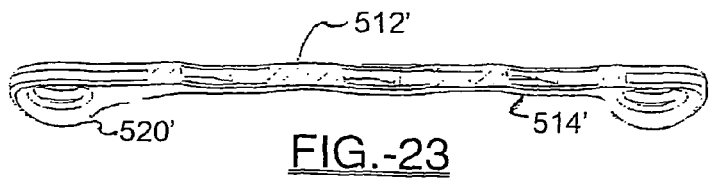
FIG. 23 is a cross section of the plate of FIG. 22 taken along line 23-23.
Figure 24:
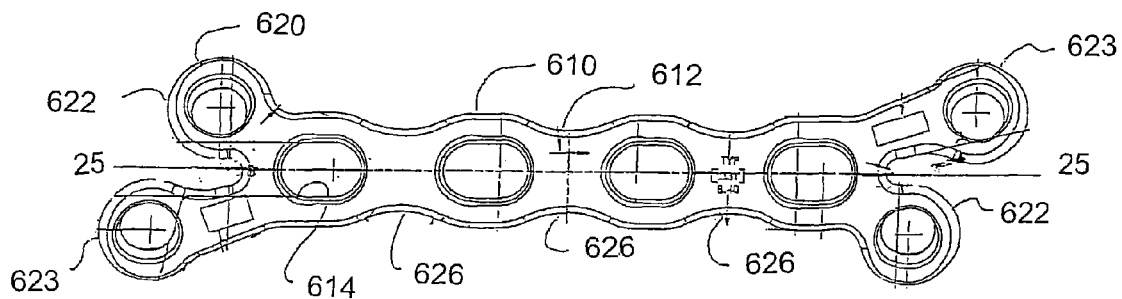
FIG. 24 is a top view of an alpha version of a sixth embodiment of a plate in accordance with the invention.
Figure 25:
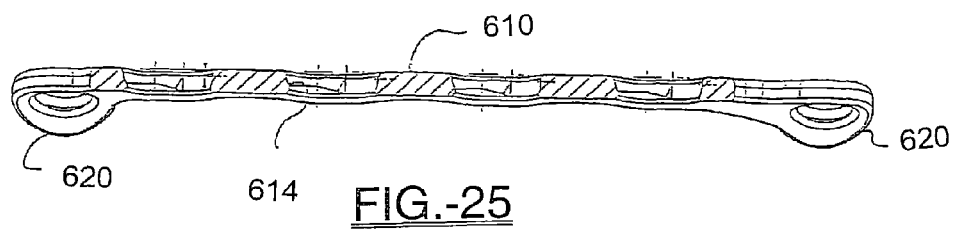
FIG. 25 is a cross section of the plate of FIG. 24 taken along line 25-25.
Figure 26:
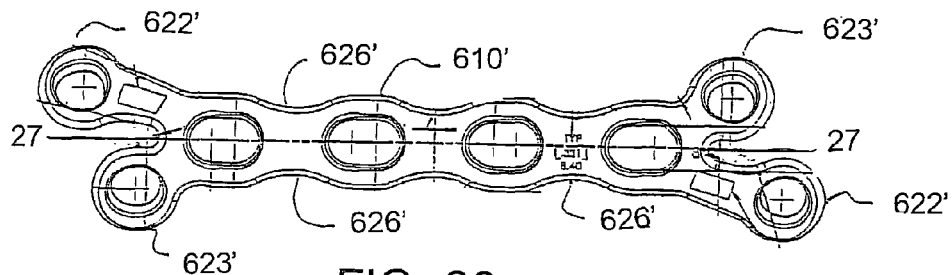
FIG. 26 is a top view of the beta version of the sixth embodiment of the plate in accordance with the invention.
Figure 27:
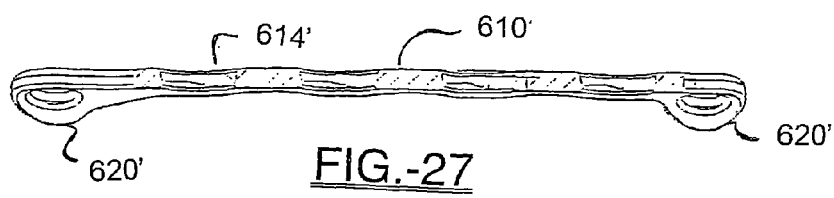
FIG. 27 is a cross section of the plate of FIG. 26 taken along line 27-27.
Figure 28:
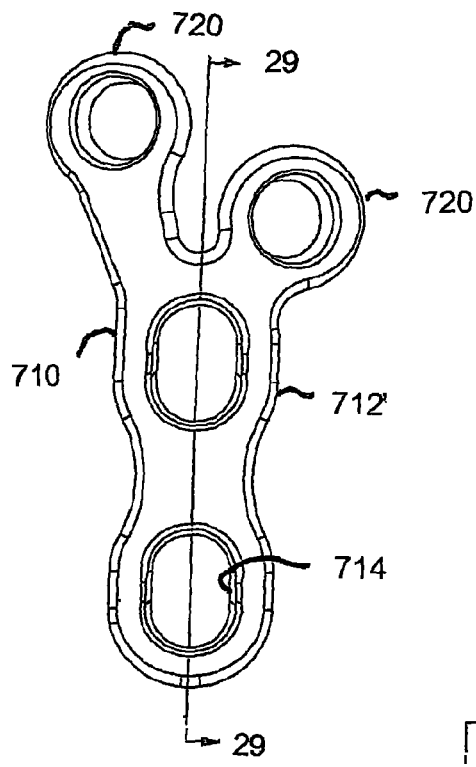
FIG. 28 is a top view of an alpha version of a seventh embodiment of a plate in accordance with the invention.
Figure 29:
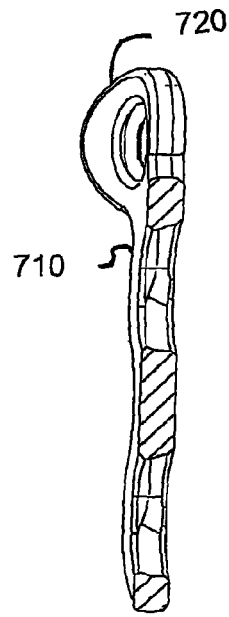
FIG. 29 is a cross section of the plate of FIG. 28 taken along line 29-29.
Figure 30:
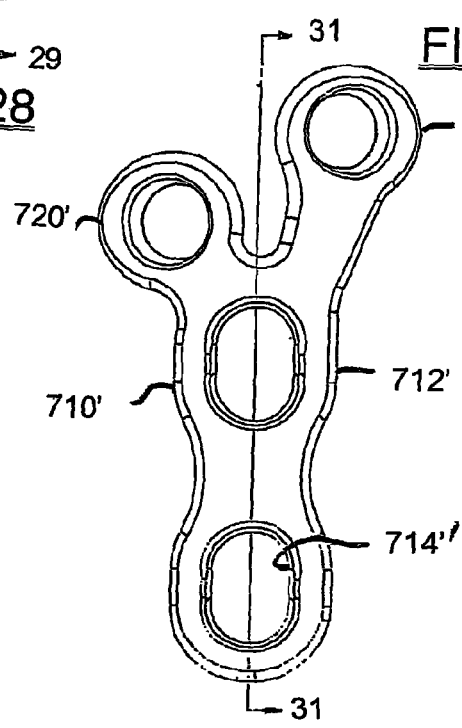
FIG. 30 is a top view of the beta version of the seventh embodiment of the plate in accordance with the invention.
Figure 31:
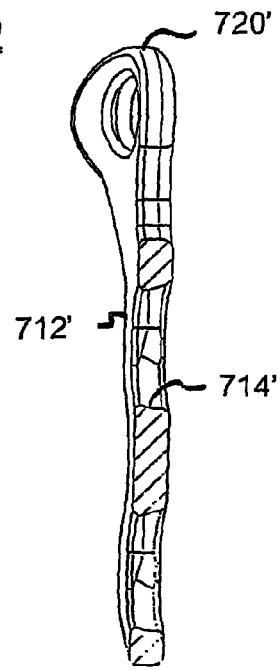
FIG. 31 is a cross section of the plate of FIG. 30 taken along line 31-31.

FIGS. 12 through 14 illustrate an embodiment of the plate 310, 310' with a shorter trunk 312, 312' that serves principally to join the two ends bearing the arms 320, 320' and including a single narrowed waist area 326, 326'. The arms 320, 320' each include screw holes 324, 324' which are rounded and provide the option of conical multi-axis fixation as shown and described for the first embodiment. FIGS. 16 through 19 illustrate an embodiment of a plate 410, 410' having two opposing pairs of arms 420, 420' each including the multi-axis screw hole 424 and having a relatively short trunk portion 412, 412' having a single compression slot 414, 414'. FIGS. 20 through 23 illustrate both the alpha and beta version of an embodiment of the plate 510, 510' which have the pairs of asymmetrical arms 520, 520' and including a central trunk area 512, 512' with three compression slots 514, 514' separated by narrowed waist areas 526, 526'. FIGS. 24 through 27 illustrate both the alpha and beta version of an embodiment of the plate 610, 610' which have the corresponding diagonally opposing arms 622 and 623, and 622', and 623' and including a central trunk area 612, 612' with three compression slots 614, 614' separated by narrowed waist areas 526, 526'. FIGS. 28 through 31 illustrate an alpha and beta version of the plate 710, 710' having only a single pair of arms 720, 720' and a trunk portion 712, 712' optionally having one or more compression slots 714, 714'.

While in accordance with the patent statutes, the best mode and preferred embodiment have been set forth, the scope of the invention is not limited thereto, but rather by the scope of the attached claims.

What is claimed is:

1. An orthopedic plate system comprising a plate which has a shape in the x-y planes that consists of a central trunk and a first set of a first arm and a second arm and a second set of a first arm and a second arm, the trunk including a screw hole and defining a central longitudinal axis extending between a first end and a second end, the first set of arms extending from the first end of the trunk and the second set of arms extending from the second end of the trunk each of said first and of said second set of said arms having a screw hole joined to the trunk by a linking section configured to bend relative to the trunk without deforming the screw hole and a longitudinal axis and defining an angle relative to the central longitudinal axis of the trunk and the angle of said first arm being different by from about 2° to about 20° from the angle of the second arm; and the plate having an inferior side capable of facing a bone and the inferior side including a radius of curvature in the z direction along the longitudinal axis whereby the screw hole of the first arm defines an axis the direction of which forms a convergent but non impinging angle toward the inferior side with the direction of the axis of the screw hole of the other arm for each set of arms.

2. An orthopedic plate system as set forth in claim 1 further including at least one screw which has a rounded head which mates with the screw hole of the first arm to allow a variable orientation of the axis of the screw.

3. An orthopedic plate system as set forth in claim 2 where the variable orientation is a conical shape relative to an axis defined by the screw hole and defines an angle of at least 20°.

4. An orthopedic plate system as set forth in claim 3 where the variable orientation is a conical shape relative to an axis defined by the screw hole and defines an angle of at least 25°.

5. An orthopedic plate system as set forth in claim 1 wherein one or more of the screw holes is threaded.

6. A surgical plate system comprising
a pre-contoured X shaped plate that has an inferior surface and which has a concentric superior surface, the plate having a trunk having a linear medial longitudinal axis along the superior surface extending between a first end and a second end, and the inferior surface of the trunk defining a curve transverse to the medial axis and the trunk having a first end and an opposing second end, and the plate having a first pair of a first arm and a second arm extending from the first end of the trunk and a second pair of a first arm and a second arm extending from the second end of the trunk, the inferior surface of the first arm and of the second arm following the same curve as the inferior surface of the trunk, the plate consisting of the trunk and the first pair of arms and the second pair of arms;
the first arm having an ear with at least one screw hole defining a first screw axis perpendicular to a tangent to the top surface of the first ear, the first ear being attached to the trunk by a linking section having a waist, a first angle and a first length being defined by a line from the center of the first arm screw hole to the intersection of the medial longitudinal axis of the trunk;
the second arm having a second ear with at least one second screw hole defining a second screw axis perpendicular to a tangent to the top surface of the second ear, the second ear being attached to the trunk by a linking section having a waist, a second angle and a second length being defined by a line from the center of the second arm screw hole to the intersection of the medial longitudinal axis of the trunk; and
the first angle and the first length being different from the second angle and the second length whereby the first screw axis and the second screw axis converge toward the inferior side of the plate but do not intersect.

7. A surgical plate system as set forth in claim 6 wherein the curve is constant along the medial axis.

8. A surgical plate system as set forth in claim 7 wherein the curve is a portion of a circle and the plate defines a segment of a cylinder.

9. A surgical plate system as set forth in claim 6 wherein the waist of the linking section of the first arm and of the second arm is configured to bend relative to the trunk section in response to a force applied before or during surgery without deforming the screw hole.

10. A surgical plate system as set forth in claim 6 wherein the trunk has a through hole.

11. A surgical plate system as set forth in claim 10 wherein the trunk has at least two through holes and a waist area between the through holes which encourages bending of the waist area in response to a force applied before or during surgery.

12. A surgical plate system as set forth in claim 6 wherein the trunk has a compression slot.

13. A surgical plate system as set forth in claim 12 wherein the compression slot comprises a slot having an internal edge which includes a shoulder that slopes toward the inferior side of the plate as it extends away from the first end of the trunk.

14. A surgical plate system as set forth in claim 12 wherein the superior surface of the trunk includes a visual indication of the direction in which the compression slot can be used to apply compression.

15. A surgical plate system as set forth in claim 6 further including at least one screw having a threaded shaft and a rounded head which mates with the screw hole of the first arm to allow a variable orientation of the axis of the screw.

16. An implant system capable of being used to stabilize a small bone fracture comprising
   a pre-contoured plate which is a X-shaped plate, the plate consisting of a trunk defining a longitudinal axis with a first end and an opposing second end, and a first pair of first arm and a second arm extending from the first end of the trunk, the trunk having a constant radial curve in the z direction about the longitudinal axis, and the first arm and the second arm of the first pair following the radial curve of the trunk so as to spiral about the longitudinal axis toward each other and a second pair of first arm and a second arm extending from the second end of the trunk and the first arm and the second arm of the second pair following the radial curve of the trunk so as to spiral about the longitudinal axis toward each other;
   each of the first arms having an ear with at least one screw hole defining a first screw axis, the first ear being attached to the trunk by a linking section having a waist, a first angle and a first length being defined by a line from the center of the first arm screw hole to the intersection of the longitudinal axis of the trunk, and the linking section waist being configured to bend relative to the trunk section without deforming the screw hole;
   each of the second arms having a second ear with at least one second screw hole defining a second screw axis, the second ear being attached to the trunk by a linking section having a waist, a second angle and a second length being defined by a line from the center of the second arm screw hole to the intersection of the longitudinal axis of the trunk, the linking section waist being configured to bend relative to the trunk section without deforming the through hole;
   the first angle and the first length being different from the second angle and the second length whereby the first screw axis and the second screw axis converge toward the inferior side of the plate but do not intersect; and
   the first arm of the first pair diagonally opposing the first arm of the second pair.

17. An implant system as set forth in claim 16 wherein the radial curve is constant along the longitudinal axis.

18. An implant system as set forth in claim 17 wherein the plate defines a segment of a cylinder.

19. An implant system as set forth in claim 16 wherein the trunk has a through hole.

20. An implant system as set forth in claim 19 wherein the trunk has at least two through holes and a waist area between the through holes which encourages bending of the waist area in response to a force applied before or during surgery.

21. An implant system as set forth in claim 16 wherein the trunk has a compression slot.

22. An implant system as set forth in claim 21 wherein the compression slot comprises a slot having an internal edge which includes a shoulder that slopes toward the inferior side of the plate as it extends away from the first end of the trunk.

23. An implant system as set forth in claim 21 wherein the superior surface of the trunk includes a visual indication of the direction in which the compression slot can be used to apply compression.

24. An implant system as set forth in claim 16 further including at least one screw having a threaded shaft and a rounded head which mates with the screw hole of the first arm to allow a variable orientation of the axis of the screw.

* * * * *